(12) United States Patent
Patel et al.

(10) Patent No.: US 6,238,886 B1
(45) Date of Patent: May 29, 2001

(54) COMPOUNDS

(75) Inventors: Lisa Patel, London; Colin Houston MacPhee, Letchworth, both of (GB)

(73) Assignee: SmithKline Beecham plc, Middlesex (GB)

( * ) Notice: Subject to any disclaimer, the term of this patent is extended or adjusted under 35 U.S.C. 154(b) by 0 days.

(21) Appl. No.: 09/251,372

(22) Filed: Feb. 16, 1999

(30) Foreign Application Priority Data

Feb. 16, 1998 (GB) .................................................. 9803290
Jan. 14, 1999 (GB) .................................................. 9900823

(51) Int. Cl.$^7$ .............................. C12P 21/02; C12N 9/12; C12N 1/20; C12N 1/00; C07H 21/04
(52) U.S. Cl. ..................... 435/69.2; 435/194; 435/252.3; 435/317.1; 435/320.1; 435/366; 536/23.5; 536/23.2
(58) Field of Search .................................. 435/194, 69.2, 435/317.1, 252.3, 320.1, 366; 536/23.2, 23.5

(56) References Cited

U.S. PATENT DOCUMENTS 5,856,132 * 1/1999 Stephens et al. .................... 435/69.2

OTHER PUBLICATIONS

GenBank accession AA565708 (Sep. 8, 1997).*
GenBank accession N53376 (Feb. 15, 1996).*
GenBank accession H78865 Nov. 9, 1995).*
GenBank accession N58477 (Jan. 28, 1997).*
GenBank Accession No. D90914: AB001339.
GenBank Accession No. AC003695.
GenBank Accession No. AC002091.
GenBank Accession No. W23946.
GenBank Accession No. AA506305.
GenBank Accession No. Y10742.
GenBank Accession No. A1209071.
GenBank Accession No. A1209070.
GenBank Accession No. A1224130.
GenBank Accession No. AA355273.
Stephens et al, "The Gssy Sensitivity of a P13K Is Dependent upon a Tightly Associated Adaptor, p101", Cell, vol. 89 pp. 105–114 (1997.

* cited by examiner

Primary Examiner—Elizabeth Slobodyansky
(74) Attorney, Agent, or Firm—William T. Han; Ratner & Prestia; William T. King

(57) ABSTRACT

SVP-1 polypeptides and polynucleotides and methods for producing such polypeptides by recombinant techniques are disclosed. Also disclosed are methods for utilizing SVP-1 polypeptides and polynucleotides in therapy, and diagnostic assays for such.

15 Claims, No Drawings

COMPOUNDS

FIELD OF THE INVENTION

This invention relates to newly identified polypeptides and polynucleotides encoding such polypeptides, to their use in therapy and in identifying compounds which may be agonists, antagonists and /or inhibitors which are potentially useful in therapy, and to production of such polypeptides and polynucleotides.

BACKGROUND OF THE INVENTION

The drug discovery process is currently undergoing a fundamental revolution as it embraces 'functional genomics', that is, high throughput genome- or gene-based biology. This approach as a means to identify genes and gene products as therapeutic targets is rapidly superceding earlier approaches based on 'positional cloning'. A phenotype, that is a biological function or genetic disease, would be identified and this would then be tracked back to the responsible gene, based on its genetic map position.

Functional genomics relies heavily on high-throughput DNA sequencing technologies and the various tools of bioinformatics to identify gene sequences of potential interest from the many molecular biology databases now available. There is a continuing need to identify and characterise further genes and their related polypeptides/proteins, as targets for drug discovery.

SUMMARY OF THE INVENTION

The present invention relates to p101 adaptor protein splice variants, SVP-1, in particular SVP-1 polypeptides and SVP-1 polynucleotides, recombinant materials and methods for their production. In another aspect, the invention relates to methods for using such polypeptides and polynucleotides, including the treatment of disease states that involve leucocyte activation and infiltration including inflammatory diseases such as COPD, ARDS, arthritis and psoriasis among others. In a further aspect, the invention relates to methods for identifying agonists and antagonists/inhibitors using the materials provided by the invention, and treating conditions associated with SVP-1 imbalance with the identified compounds In a still further aspect, the invention relates to diagnostic assays for detecting diseases associated with inappropriateSVP-1 activity or levels.

DESCRIPTION OF THE INVENTION

In a first aspect, the present invention relates to SVP-1 polypeptides. Such peptides include isolated polypeptides comprising an amino acid sequence which has at least 95% identity, preferably at least 97–99% identity, to that of SEQ ID NO:2 over the entire length of SEQ ID NO:2. Such polypeptides include those comprising the amino acid of SEQ ID NO:2.

Further peptides of the present invention include isolated polypeptides in which the amino acid sequence has at least 95% identity, preferably at least 97–99% identity, to the amino acid sequence of SEQ ID NO:2 over the entire length of SEQ ID NO:2. Such polypeptides include the polypeptide of SEQ ID NO:2.

Further peptides of the present invention include isolated polypeptides encoded by a polynucleotide comprising the sequence contained in SEQ ID NO:1.

Polypeptides of the present invention are believed to be members of the adaptor protein family of polypeptides. They are therefore of interest because the p101 adaptor protein is required for the G protein-dependent activation of a unique phosphatidylinositol-3-kinase (PI3K) subtype which controls the production of phosphoinositides specifically phosphorylated at the D3 position of the inositol ring. Phosphatidylinositol-3,4,5-trisphosphate (PIP3), for example, is a known important second messenger. This PI3 kinase is directly activated by G protein beta-gamma subunits, whilst PIP3 is thought to regulate several important events in leukocytes, including adherence, migration, and degranulation. Hence, inhibition of PIP3 accumulation by, for example, preventing the binding of G-beta gamma to p101/PI3 kinase, would be of benefit in various disease states that involve leukocyte activation. These properties are hereinafter referred to as "SVP-1 activity" or "SVP-1 polypeptide activity" or "biological activity of human SVP-1". Also included amongst these activities are antigenic and immunogenic activities of said SVP-1 polypeptides, in particular the antigenic and immunogenic activities of the polypeptide of SEQ ID NO:2. Preferably, a polypeptide of the present invention exhibits at least one biological activity of human SVP-1.

The polypeptides of the present invention may be in the form of the "mature" protein or may be a part of a larger protein such as a precursor or a fusion protein. It is often advantageous to include an additional amino acid sequence which contains secretory or leader sequences, prosequences, sequences which aid in purification such as multiple histidine residues, or an additional sequence for stability during recombinant production.

The present invention also includes variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, 1–3, 1–2 or 1 amino acids are substituted, deleted, or added in any combination.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

In a further aspect, the present invention relates to SVP-1 polynucleotides. Such polynucleotides include isolated polynucleotides comprising a nucleotide sequence encoding a polypeptide which has at least 95% identity to the amino acid sequence of SEQ ID NO.2, over the entire length of SEQ ID NO:2. In this regard, polypeptides which have at least 97% identity are highly preferred, whilst those with at least 98–99% identity are more highly preferred, and those with at least 99% identity are most highly preferred. Such polynucleotides include a polynucleotide comprising the nucleotide sequence contained in SEQ ID NO:1 encoding the polypeptide of SEQ ID NO:2.

Further polynucleotides of the present invention include isolated polynucleotides comprising a nucleotide sequence that has at least 95% identity to a nucleotide sequence encoding a polypeptide of SEQ ID NO:2, over the entire coding region. In this regard, polynucleotides which have at least 97% identity are highly preferred, whilst those with at least 98–99% identity are more highly preferred, and those with at least 99% identity are most highly preferred.

Further polynucleotides of the present invention include isolated polynucleotides comprising a nucleotide sequence which has at least 95% identity to SEQ ID NO:1 over the entire length of SEQ ID NO:1. In this regard, polynucleotides which have at least 97% identity are highly preferred, whilst those with at least 98–99% identity are more highly preferred, and those with at least 99% identity are most highly preferred. Such polynucleotides include a polynucleotide comprising the polynucleotide of SEQ ID NO:1 as well as the polynucleotide of SEQ ID NO:1.

The invention also provides polynucleotides which are complementary to all the above described polynucleotides.

The nucleotide sequence of SEQ ID NO:1 is a splice variant of human p101 (European Patent Application No: EP98306696.0; SmithKline Beecham) which lacks exons 6, 7, 9 and 10. The full-length nucleotide sequence of human p101 is given in SEQ ID NO:5. SEQ ID NO:5 is a cDNA sequence and comprises a polypeptide encoding sequence (nucleotide 1 to 3630, Exon 1 (1–106), Exon 2 (107–205), Exon 3 (206–265), Exon 4 (266–414), Exon 5 (415–479), Exon 6 (480–648), Exon 7 (649–810), Exon 8 (811–894), Exon 9 (895–1616), Exon 10 (1617–1778), Exon 11 (1779–1907), Exon 12 (1908–2037), Exon 13 (2038–2129), Exon 14 (2) encoding a polypeptide of 880 amino acids, the polypeptide of SEQ ID NO:6.

SEQ ID NO:1 is a cDNA sequence and comprises a polypeptide encoding sequence (nucleotide 295 to 1722) encoding a polypeptide of 475 amino acids, the polypeptide of SEQ ID NO:2. The nucleotide sequence encoding the polypeptide of SEQ ID NO:2 may be identical to the polypeptide encoding sequence contained in SEQ ID NO:1 or it may be a sequence other than the one contained in SEQ ID NO:1, which, as a result of the redundancy (degeneracy) of the genetic code, also encodes the polypeptide of SEQ ID NO:2. The polypeptide of the SEQ ID NO:2 is structurally related to other proteins of the adaptor protein family, having homology and/or structural similarity with pig (S.scrofa) p101, (L. R. Stephens et al., Cell 89, p105–114).

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one SVP-1 activity.

The present invention also relates to partial or other polynucleotide and polypeptide sequences which were first identified prior to the determination of the corresponding full length sequences of SEQ ID NO:1 and SEQ ID NO:2.

Accordingly, in a further aspect, the present invention provides for an isolated polynucleotide which:
  (a) comprises a nucleotide sequence which has at least 95% identity, preferably at least 97–99% identity to SEQ ID NO:3 over the entire length of SEQ ID NO:3;
  (b) a nucleotide sequence which has at least 95% identity, preferably at least 97–99% identity, to SEQ ID NO:3 over the entire length of SEQ ID NO:3;
  (c) the polynucleotide of SEQ ID NO:3; or
  (d) a nucleotide sequence encoding a polypeptide which has at least 95% identity, preferably at least 97–99% identity, to the amino acid sequence of SEQ ID NO:4, over the entire length of SEQ ID NO:4;
as well as the polynucleotide of SEQ ID NO:3.

The present invention further provides for a polypeptide which:
  (a) comprises an amino acid sequence which has at least 95% identity, preferably at least 97–99% identity, to that of SEQ ID NO:4 over the entire length of SEQ ID NO:4;
  (b) has an amino acid sequence which is at least 95% identity, preferably at least 97–99% identity, to the amino acid sequence of SEQ ID NO:4 over the entire length of SEQ ID NO:4;
  (c) comprises the amino acid of SEQ ID NO:4; and
  (d) is the polypeptide of SEQ ID NO:4;
as well as polypeptides encoded by a polynucleotide comprising the sequence contained in SEQ ID NO:3.

The nucleotide sequence of SEQ ID NO:3 and the peptide sequence encoded thereby are derived from EST (Expressed Sequence Tag) sequences. It is recognised by those skilled in the art that there will inevitably be some nucleotide sequence reading errors in EST sequences (see Adams, M. D. et al, Nature 377 (supp) 3, 1995). Accordingly, the nucleotide sequence of SEQ ID NO:3 and the peptide sequence encoded therefrom are therefore subjec to the same inherent limitations in sequence accuracy. Furthermore, the peptide sequence encoded by SEQ ID NO:3 comprises a region of identity or close homology and/or close structural similarity (for example a conservative amino acid difference) with the closest homologous or structurally similar protein.

Polynucleotides of the present invention may be obtained, using standard cloning and screening techniques, from a cDNA library derived from mRNA in cells of human peripheral blood leucocytes, (Sambrook et al., Molecular Cloning: A Laboratory Manual, 2nd Ed., Cold Spring Harbor Laboratory Press, Cold Spring Harbor, N.Y.(1989)). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself; or the coding sequence for the mature polypeptide in reading flame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989)86:821–824, or is an HA tag. The polynucleotide may also contain non-coding 5'and 3'sequences, such as transcribed, non-translated sequences, splicing and polyadenylation signals, ribosome binding sites and sequences that stabilize mRNA.

Further embodiments of the present invention include polynucleotides encoding polypeptide variants which comprise the amino acid sequence of SEQ ID NO:2 and in which several, for instance from 5 to 10, 1 to 5, 1 to 3, 1to 2 or 1, amino acid residues are substituted, deleted or added, in any combination.

Polynucleotides which are identical or sufficiently identical to a nucleotide sequence contained in SEQ ID NO:1, may be used as hybridization probes for cDNA and genomic DNA or as primers for a nucleic acid amplification (PCR) reaction, to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO:1. Typically these nucleotide sequences are 70% identical, preferably 80% identical, more preferably 90% identical, most preferably 95% identical to that of the referent. The probes or primers will generally comprise at least 15 nucleotides, preferably, at least 30 nucleotides and may have at least 50 nucleotides. Particularly preferred probes will have between 30 and 50 nucleotides. Particularly preferred primers will have between 20 and 25 nucleotides.

A polynucleotide encoding a polypeptide of the present invention, including homologs from species other than human, may be obtained by a process which comprises the steps of screening an appropriate library under stringent hybridization conditions with a labeled probe having the sequence of SEQ ID NO:1 or a fragment thereof; and isolating full-length cDNA and genomic clones containing said polynucleotide sequence. Such hybridization techniques are well known to the skilled artisan. Preferred stringent hybridization conditions include overnight incubation at 42° C. in a solution comprising:50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA; followed by washing the filters in 0.1×SSC at about 65° C. Thus the present invention also includes polynucleotides obtainable by screening an appropriate library under stringent hybridization conditions with a labeled probe having the sequence of SEQ ID NO:1 or a fragment thereof.

The skilled artisan will appreciate that, in many cases, an isolated cDNA sequence will be incomplete, in that the region coding for the polypeptide is short at the 5' end of the cDNA. This is a consequence of reverse transcriptase, an enzyme with inherently low 'processivity' (a measure of the ability of the enzyme to remain attached to the template during the polymerisation reaction), failing to complete a DNA copy of the mRNA template during 1st strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., PNAS USA 85, 8998–9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the 'missing' 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analysed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems which comprise a polynucleotide or polynucleotides of the present invention, to host cells which are genetically engineered with such expression sytems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al, Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Preferred such methods include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as Streptococci, Staphylococci, *E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook et al., Molecular Cloning, A Laboratory Manual (supra). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during intracellular synthesis, isolation and or purification.

This invention also relates to the use of polynucleotides of the present invention as diagnostic reagents. Detection of a mutated form of the gene characterised by the polynucleotide of SEQ ID NO:1 which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled SVP-1 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (ee, e.g., Myers et al, Science (1985) 230:1242). Sequence changes at specific locations may also be revealed by nuclease protection assays, such as RNase and S1 protection or the chemical cleavage method (see Cotton et al., Proc Natl Acad Sci USA (1985) 85: 4397–4401). In another embodiment, an array of oligonucleotides probes comprising SVP-1 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability (see for example: M.Chee et al., Science, Vol 274, pp 610–613 (1996)).

The diagnostic assays offer a process for diagnosing or determining a susceptibility to the Diseases through detection of mutation in the SVP-1 gene by the methods described. In addition, such diseases may be diagnosed by methods comprising determining from a sample derived from a subject an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagonostic kit which comprises:
  (a) a polynucleotide of the present invention, preferably the nucleotide sequence of SEQ ID NO: 1, or a fragment thereof;
  (b) a nucleotide sequence complementary to that of (a);
  (c) a polypeptide of the present invention, preferably the polypeptide of SEQ ID NO:2 or a fragment thereof; or
  (d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease or suspectability to a disease, particularly disease states that involve leucocyte activation and infiltration including inflammatory diseases such as COPD, ARDS, arthritis and psoriasis among others The nucleotide sequences of the present invention are also valuable for chromosomal localisation. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

The gene of the present invention maps to human chromosome 17p12–13.1.

The nucleotide sequences of the present invention are also valuable for tissue localisation. Such techniques allow the determination of expression patterns of the human SVP-1 polypeptides in tissues by detection of the mRNAs that encode them. These techniques include in situ hybridziation techniques and nucleotide amplification techniques, for example PCR. Such techniques are well known in the art. Results from these studies provide an indication of the normal functions of the polypeptides in the organism. In addition, comparative studies of the normal expression pattern of human SVP-1 mRNAs with that of mRNAs encoded by a human SVP-1 gene provide valuable insights into the role of mutant human SVP-1 polypeptides, or that of inappropriate expression of normal human SVP-1 polypeptides, in disease. Such inappropriate expression may be of a temporal, spatial or simply quantitative nature.

The polypeptides of the invention or their fragments or analogs thereof, or cells expressing them, can also be used as immunogens to produce antibodies immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, analogs or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole el al., Monoclonal Antibodies and Cancer Therapy, 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography.

Antibodies against polypeptides of the present invention may also be employed to treat the Diseases, amongst others.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Another aspect of the invention relates to a method for inducing an immunological response in a mammal which comprises inoculating the mammal with a polypeptide of the present invention, adequate to produce antibody and/or T cell immune response to protect said animal from the Diseases hereinbefore mentioned, amongst others. Yet another aspect of the invention relates to a method of inducing immunological response in a mammal which comprises, delivering a polypeptide of the present invention via a vector directing expression of the polynucleotide and coding for the polypeptide in vivo in order to induce such an immunological response to produce antibody to protect said animal from diseases.

A further aspect of the invention relates to an immunological/vaccine formulation (composition) which, when introduced into a mammalian host, induces an immunological response in that mammal to a polypeptide of the present invention wherein the composition comprises a polypeptide or polynucleotide of the present invention The vaccine formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention are responsible for one or more biological functions, including one or more disease states, in particular the Diseases hereinbefore mentioned. It is therefore desirous to devise screening methods to identify compounds which stimulate or which inhibit the function of the polypeptide. Accordingly, in a further aspect, the present invention provides for a method of screening compounds to identify those which stimulate or which inhibit the function of the polypeptide. In general, agonists or antagonists may be employed for therapeutic and prophylactic purposes for such Diseases as hereinbefore mentioned. Compounds may be identified from a variety of sources, for example, cells, cell-free preparations, chemical libraries, and natural product mixtures. Such agonists, antagonists or inhibitors so-identified may be natural or modified substrates, ligands, receptors, enzymes, etc., as the case may be, of the polypeptide; or may be structural or functional mimetics thereof(see Coligan et al., Current Protocols in Immunology 1(2):Chapter 5(1991)).

The screening method may simply measure the binding of a candidate compound to the polypeptide, or to cells or membranes bearing the polypeptide, or a fusion protein thereof by means of a label directly or indirectly associated with the candidate compound. Alternatively, the screening method may involve competition with a labeled competitor. Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Constitutively active polypeptides may be employed in screening methods for inverse agonists or inhibitors, in the absence of an agonist or inhibitor, by testing whether the candidate compound results in inhibition of activation of the polypeptide. Further, the screening methods may simply comprise the steps of mixing a candidate compound with a solution containing a polypeptide of the present invention, to form a mixture, measuring SVP-1 activity in the mixture, and comparing the SVP-1 activity of the mixture to a standard. Fusion proteins, such as those made from Fc portion and SVP-1 polypeptide, as hereinbefore described, can also be used for high-throughput screening assays to identify antagonists for the polypeptide of the present invention (see D. Bennett et al., J Mol Recognition, 8:52–58 (1995); and K. Johanson et al., J Biol Chem, 270(16):9459–9471 (1995)).

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide(also called antagonist or agonist, respectively) from suitably manipulated cells or tissues.

The polypeptide may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide which compete with the binding of the polypeptide to its receptors, if any. Standard methods for conducting such assays are well understood in the art.

Examples of potential polypeptide antagonists include antibodies or, in some cases, oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypeptide of the present invention but do not elicit a response, so that the activity of the polypeptide is prevented.

Thus, in another aspect, the present invention relates to a screening kit for identifying agonists, antagonists, ligands, receptors, substrates, enzymes, etc. for polypeptides of the present invention; or compounds which decrease or enhance the production of such polypeptides, which comprises:

(a) a polypeptide of the present invention;

(b) a recombinant cell expressing a polypeptide of the present invention;

(c) a cell membrane expressing a polypeptide of the present invention; or (d) antibody to a polypeptide of the present invention;

which polypeptide is preferably that of SEQ ID NO:2.

It will be appreciated that in any such kit, (a), (b), (c) or (d) may comprise a substantial component.

It will be readily appreciated by the skilled artisan that a polypeptide of the present invention may also be used in a method for the structure-based design of an agonist, antagonist or inhibitor of the polypeptide, by:

(a) determining in the first instance the three-dimensional structure of the polypeptide;

(b) deducing the three-dimensional structure for the likely reactive or binding site(s) of an agonist, antagonist or inhibitor;

(c) synthesing candidate compounds that are predicted to bind to or react with the deduced binding or reactive site; and (d) testing whether the candidate compounds are indeed agonists, antagonists or inhibitors.

It will be further appreciated that this will normally be an iterative process.

In a further aspect, the present invention provides methods of treating abnormal conditions such as, for instance, disease states that involve leucocyte activation and infiltration including inflammatory diseases such as COPD, ARDS, arthritis and psoriasis among others related to either an excess of, or an under-expression of, SVP-1 polypeptide activity.

If the activity of the polypeptide is in excess, several approaches are available. One approach comprises administering to a subject in need thereof an inhibitor compound (antagonist) as hereinabove described, optionally in combination with a pharmaceutically acceptable carrier, in an amount effective to inhibit the function of the polypeptide, such as, for example, by blocking the binding of ligands, substrates, receptors, enzymes, etc., or by inhibiting a second signal, and thereby alleviating the abnormal condition. In another approach, soluble forms of the polypeptides still capable of binding the ligand, substrate, enzymes, receptors, etc. in competition with endogenous polypeptide may be administered. Typical examples of such competitors include fragments of the SVP-1 polypeptide.

In still another approach, expression of the gene encoding endogenous SVP-1 polypeptide can be inhibited using expression blocking techniques. Known such techniques involve the use of antisense sequences, either internally generated or externally administered (see, for example, O'Connor, J Neurochem (1991) 56:560 in Oligodeoxynucleotides as Antisense Inhibitors of Gene Expression, CRC Press, Boca Raton, Fla. (1988)). Alternatively, oligonucleotides which form triple helices ("triplexes") with the gene can be supplied (see, for example, Lee et al., Nucleic Acids Res (1979) 6:3073; Cooney et al., Science (1988) 241:456; Dervan et al., Science (1991) 251:1360). These oligomers can be administered per se or the relevant oligomers can be expressed in vivo. Synthetic antisense or triplex oligonucleotides may comprise modified bases or modified backbones. Examples of the latter include methylphosphonate, phosphorothioate or peptide nucleic acid backbones. Such backbones are incorporated in the antisense or triplex oligonucleotide in order to provide protection from degradation by nucleases and are well known in the art. Antisense and triplex molecules synthesised with these or other modified backbones also form part of the present invention.

In addition, expression of the human SVP-1 polypeptide may be prevented by using ribozymes specific to the human SVP-1 mRNA sequence. Ribozymes are catalytically active RNAs that can be natural or synthetic (see for example Usman, N, et al., Curr. Opin. Struct. Biol (1996) 6(4), 527–33.) Synthetic ribozymes can be designed to specifically cleave human SVP-1 mRNAs at selected positions thereby preventing translation of the human SVP-1 mRNAs into functional polypeptide. Ribozymes may be synthesised with a natural ribose phosphate backbone and natural bases, as normally found in RNA molecules. Alternatively the ribosymes may be synthesised with non-natural backbones to provide protection from ribonuclease degradation, for example, 2'-O-methyl RNA, and may contain modified bases.

For treating abnormal conditions related to an under-expression of SVP-1 and its activity, several approaches are also available. One approach comprises administering to a subject a therapeutically effective amount of a compound which activates a polypeptide of the present invention, i.e., an agonist as described above, in combination with a pharmaceutically acceptable carrier, to thereby alleviate the abnormal condition. Alternatively, gene therapy may be employed to effect the endogenous production of SVP-1 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For an overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996). Another approach is to administer a therapeutic amount of a polypeptide of the present invention in combination with a suitable pharmaceutical carrier.

In a further aspect, the present invention provides for pharmaceutical compositions comprising a therapeutically effective amount of a polypeptide, such as the soluble form of a polypeptide of the present invention, agonist/antagonist peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, and the like.

The dosage range required depends on the choice of peptide or other compounds of the present invention, the route of administration, the nature of the formulation, the nature of the subject's condition, and the judgment of the attending practitioner. Suitable dosages, however, are in the range of 0.1–100 $\mu$g/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Polynucleotide and polypeptide sequences form a valuable information resource with which to identify further sequences of similar homology. This is most easily facilitated by storing the sequence in a computer readable medium and then using the stored data to search a sequence database using well known searching tools, such as those in GCG and Lasergene software packages. Accordingly, in a her aspect, the present invention provides for a computer readable medium having stored thereon a polynucleotide comprising the sequence of SEQ ID NO:1 and/or a polypeptide sequence encoded thereby.

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, Proteins—Structure and Molecular Properties, 2nd Ed., T. E. Creighton, W. H. Freeman and Company, N.Y., 1993; Wold, F., Post-translational Protein Modifications: Perspectives and Prospects, pgs. 1–12 in Post-translational Covalent Modification of Proteins, B. C. Johnson, Ed., Academic Press, N.Y., 1983; Seifter et al., "Analysis for protein modifications and nonprotein cofactors", Meth Enzymol (1990) 182:626–646 and Rattan et al., "Protein Synthesis: Post-translational Modifications and Aging", Ann NY Acad Sci (1992) 663:48–62).

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, N.Y., 1988; *Biocomputing: Informatics and Genome Projects*, Smith, D. W., ed., Academic Press, N.Y., 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48:1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1):387 (1984)), BLASTP, BLASTN, and FASTA (Atschul, S.F. et al., *J Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Preferred parameters for polypeptide sequence comparison include the following:

1) Algorithm: Needleman and Wunsch, J. Mol Biol. 48: 443–453 (1970)

Comparison matrix: BLOSSUM62 from Hentikoff and Hentikoff, Proc. Natl. Acad. Sci. USA. 89:10915–10919 (1992)

Gap Penalty: 12

Gap Length Penalty:4

A program useful with these parameters is publicly available as the "gap" program from Genetics Computer Group, Madison Wis. The aforementioned parameters are the default parameters for peptide comparisons (along with no penalty for end gaps).

Preferred parameters for polynucleotide comparison include the following:

1) Algorithm: Needleman and Wunsch, J. Mol Biol. 48: 443–453 (1970)

Comparison matrix: matches=+10, mismatch =0

Gap Penalty:50

Gap Length Penalty:3

Available as: The "gap" program from Genetics Computer Group, Madison, Wis. These are the default parameters for nucleic acid comparisons.

By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1 by the numerical percent of the respective percent identity(divided by 100) and subtracting that product from said total number of nucleotides in SEQ ID NO:1, or:

$$n_n \leq x_n - (x_n \cdot 19 \cdot y),$$

wherein $n_n$ is the number of nucleotide alterations, $x_n$ is the total number of nucleotides in SEQ ID NO:1, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity(divided by 100) and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, and y is, for instance 0.70 for 70%, 0.80 for 80%, 0.85 for 85% etc., and wherein any non-integer product of $x_a$ and y is rounded down to the nearest integer prior to subtracting it from $x_a$.

"Homolog" is a generic term used in the art to indicate a polynucleotide or polypeptide sequence possessing a high degree of sequence relatedness to a subject sequence. Such relatedness may be quantified by determining the degree of identity and/or similarity between the sequences being compared as hereinbefore described. Falling within this generic term are the terms "ortholog", meaning a polynucleotide or polypeptide that is the functional equivalent of a polynucleotide or polypeptide in another species, and "paralog" meaning a functionally similar sequence when considered within the same species.

"Fusion protein" refers to a protein encoded by two, often unrelated, fused genes or fragments thereof. In one example, EP-A-0 464 discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 0232 262]. On the other hand, for some uses it would be desirable to be able to delete the Fc part after the fusion protein has been expressed, detected and purified.

EXAMPLE

Expression patterns of SVP-1 were investigated using Northern blot analysis, using standard methods (for example Sambrook et al., Molecular Cloning: A Laboratory Manual, 2nd Ed., Cold Spring Harbor Laboratory Press, Cold Spring Harbor, N.Y.(1989), and Taqman fluorescent PCR (Perkin Elmer). Northern blots showed that the SVP-1 splice variant transcript is approximately 8 kb in size. The Northern blot data detected expression in peripheral blood leucocytes, lymph node and bone marrow.

Taqman was used to further investigate the expression of SVP-1 in leucocytes observed from the Northern blot data. The Taqman analysis was carried out according to the manufacturers instructions using the following oligonucleotides:

SVP1 labelled probe:5'CAAAACCAGGGAAGCTCCATGCCA 3'

SVP1 forward primer:5'CGCAGCTCCACCGTACACT 3'

SVP1 reverse primer:5'TGGCGACAGGGATGGG 3'

Taqman PCR was carried out on a set of human leucocytic cells, including lymphocytes, neutrophils, platelets and monocytes. The signal was then normalised to 3 different housekeeping genes-glyceraldehyde-3-phosphate dehydrogenase (GAPDH), hypoxanthine ribosyl tranferase (HPRT) and acidic ribosomal phoshoprotein P0 (36B4). Expression of SVP-1 was detected in monocytes, macrophages and lymphocytes and at a higher level in platelets and neutrophils. The highest levels of expression were found in activated neutrophils. Expression of SVP-1 was also detected in a microglial cell line (C13), with a dramamatic increase following stimulation of the cells with IL-1α.

Expression of SVP-1 in monocytes decreased during culturing, with the presence of GMCSF further reducing expression levels, whilst in neutrophils the expression of SVP-1 was found to decrease after 1 hour in culture and the increase again after 4 hours in culture.

All publications, including but not limited to patents and patent applications, cited in this specification are herein incorporated by reference as if each individual publication were specifically and individually indicated to be incorporated by reference herein as though fully set forth.

```
SEQUENCE INFORMATION
SEQ ID NO:1
CCCTTTCCACCTCTCTGCTCCCATTCCTGACCCCTTACTTCCCACACCTCTGTCCCGTTCTGCTGCAGGGG

TGCTCTGTCCTGCCACTCAGATGTGGCCCTCCAGATGCCATTCCTACCCTGGAGGCAGCTGTAAGGCCCCT

GGTCCTGTTTCCACAGCACCTGAGCTATAGCTGGGCTGGGCTGATCGCGCTGCACTGTGAGCACCTGTTGT

CTTTACTGGACCAGGTGCTCTCTGGGAAAGGAGCTCGACAAGCTGACCGGCGTCTGTCCCCCATGCAGGCG

ATGACCCAGGATGCAGCCAGGGGCCACGACATGCACGGAGGACCGCATCCAGCATGCCCTGGAACGCTGCC

TGCATGGACTCAGCCTCAGCCGCCGCTCCACCTCCTGGTCAGCTGGGCTGTGTCTGAACTGCTGGAGCCTG

CAGGAGCTGGTCAGCAGGGACCCGGGCCACTTCCTTATCCTCCTTGAGCAGATCCTGCAGAAGACCCGAGA

GGTCCAGGAGAAGGGCACCTACGACCTGCTCACCCCGCTGGCCCTGCTCTTCTATTCCACTGTTCTTTGTA

CACCACACTTCCCACCAGACTCGGATCTCCTTCTGAAGGCAGCCAGCACCTACCACCGGTTCCTGACCTGG

CCTGTTCCTTACTGCAGCATCTGCCAGGAGCTGCTCACCTTCATTGATGCTGAACTCAAGGCCCCAGGGAT

CTCCTACCAG
```

-continued

AGACTGGTGAGGGCTGAGCAGGGCCTGCCCATCAGGAGTCACCGCAGCTCCACCACACTGCAAAACCAGGG

AAGCTTCATACCATCCCCATCCCTGTCGCCAGGTGCTACACCTACAGCTGGAGCCAGGACAGCTTTGGAGC

TGGGCACCACCCCATGGGAGGAGAGCACCAATGGCATCTCCCACTACCTCGGCATGCTGGACCCCTGGTAT

GAGCGCAATGTACTGGGCCTCATGCACCTGCCCCCTGAAGTCCTGTGCCAGCAGTCCCTGAAGGCTGAAGC

CCAGGCCCTGGAGGGCTCCCCAACCCAGCTGCCCATCCTGGCTGACATGCTACTCTACTACTGCCGCTTTG

CCGCCAGACCGGTGCTGCTGCAAGTCTATCAGACCGAGCTGACCTTCATCACTGGGGAGAAGACGACAGAG

ATCTTCATCCACTCCTTGGAGCTGGGTCACTCCGCTGCCACACGTGCCATCAAGGCGTCAGGTCCTGGCAG

CAAGCGGCTGGGCATCGATGGCGACCGGGAGGCTGTTCCTCTAACACTACAGATTATTTACAGCCAGGGGG

CCATCAGTGGACGAAGTCGCTGGAGCAACCTGGAGAAGGTCTGTACCTCCGTGAACCTCAACAAGGCCTGC

CGGAAGCAGGAGGAGCTGGATTCCAGCATGGAGGCCCTGACGCTAAACCTGACAGAAGTGGTGAAAAGGCA

GAACTCCAAA

TCCAAGAAGGGCTTTAACCAGATTAGCACATCGCAGATCAAAGTGGACAAGGTGCAGATCATCGGCTCCAA

CAGCTGCCCCTTTGCTGTGTGCCTGGACCAGGATGAGAGAAAGATCCTGCAGAGTGTAGTCAGATGTGAGG

TCTCACCGTGCTACAAGCCAGAGAAGAGCGACCTCTCCTCACCACCCCAGACGCCTCCTGACCTGCCGGCC

CAGGCCGCACCTGATCTCTGCTCCCTCCTCTGCCTGCCCATCATGACTTTCAGTGGAGCTCTGCCCTAGTG

TGGGCCCAGCGCCAGACTGGACAGAAGCCCTGGGGTCATTTCTCCAGCACTAAAATGGAGTGGAGAGTTGG

GGTGGAAATAAGACATCCTTAAAAGGTTAAATTGTCTGCAAAGCACCTAGCCCAGTGCCGAGCTCCCAGTA

GGTGTTCAGTAAAGCTTAGTGCCTGACTTTCTGAACACTGATTCCTCCTGTTTGGAGTCACTGGGATACTC

TCATTGCCGTTGGGATGTTCCTCACTCCTTCCCAGTTCGTGGCTGAGGCAGAACCCAGACTGAAGAGGGAA

GAGACATTCCAGAGGAGGATTGCCTTCGTCAGGGTAAGGGGTGGGCTGCTCAGGGGCCCTACCCTTCACCC

CCTTCTGTATCAGATTGGCCCTCCCACTCCCATCTCACTCTGCGTGTACAATCTTCCATATCCGCAAGTTC

ACTGGCACTC

TTCTGGCACCTGGGCAAGATCCCAGAACAGAGGATGGAGTGACTGGCCTCACAGAGCTTAGTGCCCGACAC

TGGTGCATGGGAAATGGTCAGCCTAGGATAGGACACGAGAGTCTGAAATTCAAAGCAACCAGCTTGAAGTG

GTTTGAGAAGCTGGAAGCAAACATGGGCTAGAGAGATAGGGCAGAAGTCAAGACGAGGATCTGGACTGATG

TGGAGAAAGTAGCCACGGAAGCATGAACTGTATCCTGCACAAAGTCCCTCTTCCCCGCCTCCTAATTCATT

ATGCCCAAAAGGCCTTACGTGAAATTCCAGCCCAGAGTACTCATGACTTGAGAGACGTGGACAGAGCCAGC

TTCTACCTTGCCTGGCCGTCTCTCCCCTGTCTTAATGTCTGCTCTTGCTCTAAGCTCCAGAAGAGTGGCGG

GCCATGTATCTTCAATATGTTTTTGCTGTATGGGCAGGTTGTCTTATTATGTGATCAACAGATGTCCAGGA

ACTAATGAGTGGAATTTAATATTATTGTCAAATAAAACTTGATTTGTCCTAT

SEQ ID NO:2

MQPGATTCTEDRIQHALERCLHGLSLSRRSTSWSAGLCLNCWSLQELVSRDPGHFLILLEQILQKTREVQE

KGTYDLLTPLALLFYSTVLCTPHFPPDSDLLLKAASTYHRFLTWPVPYCSICQELLTFIDAELKAPGISYQ

RLVRAEQGLPIRSHRSSTTLQNQGSFIPSPSLSPGATPTAGARTALELGTTPWEESTNGISHYLGMLDPWY

ERNVLGLMHLPPEVLCQQSLKAEAQALEGSPTQLPILADMLLYYCRFAARPVLLQVYQTELTFITGEKTTE

IFIHSLELGHSAATRAIKASGPGSKRLGIDGDREAVPLTLQIIYSQGAISGRSRWSNLEKVCTSVNLNKAC

RKQEELDSSMEALTLNLTEVVKRQNSKSKKGFNQISTSQIKVDKVQIIGSNSCPFAVCLDQDERKILQSVV

RCEVSPCYKPEKSDLSSPPQTPPDLPAQAAPDLCSLLCLPIMTFSGALP

SEQ ID NO:3

TTCCTTACTGCAGCATCTGCCAGGAGCTGCTCACCTTCATTGATGCTGAACTCAAGGCCCCAGGGATCTCC

-continued

TACCAGAGACTGGTGAGGGCTGAGCAGGGCCTGCCCATCAGGAGTCACCGCAGCTCCACCGTACACTGCAA

AACCAGGGAAGCTCCATgCCATCCCCATCCCTGTCGCCAGGTGCTACACCTACAGCTGGAGCCAGGACAGC

TTTGGAGCTGGGCACCACCCCATGGGAGGAGAGCACCAATGAC

SEQ ID NO:4

PYCSICQELLTFIDAELKAPGISYQRLVRAEQGLPIRSHRSSTVHCKTREAPCHPHPCRQVLHLQLEPGQL

WSWAPPHGRRAPM

SEQ ID NO:5(Full-length human p101 DNA)

ATGCAGCCAGGGGCCACGACATGCACGGAGGACCGCATCCAGCATGCCCTGGAACGCTGCCTGCATGGACT

CAGCCTCAGCCGCCGCTCCACCTCCTGGTCAGCTGGGCTGTGTCTGAACTGCTGGAGCCTGCAGGAGCTGG

TCAGCAGGGACCCGGGCCACTTCCTTATCCTCCTTGAGCAGATCCTGCAGAAGACCCGAGAGGTCCAGGAG

AAGGGCACCTACGACCTGCTCACCCCGCTGGCCCTGCTCTTCTATTCCACTGTTCTTTGTACACCACACTT

CCCACCAGACTCGGATCTCCTTCTGAAGGCAGCCAGCACCTACCACCGGTTCCTGACCTGGCCTGTTCCTT

ACTGCAGCATCTGCCAGGAGCTGCTCACCTTCATTGATGCTGAACTCAAGGCCCCAGGGATCTCCTACCAG

AGACTGGTGAGGGCTGAGCAGGGCCTGCCCATCAGGAGTCACCGCAGCTCCACCGTCACCGTGCTGCTGCT

GAACCCAGTGGAAGTGCAGGCCGAGTTCCTTGCTGTAGCCAATAAGCTGAGTACGCCCGGACACTCGCCTC

ACAGTGCCTACACCACCCTGCTCCTGCACGCCTTCCAGGCCACCTTTGGGGCCCACTGTGACGTCCCGGGC

CTGCACTGCAGGCTACAGGCCAAGACCCTGGCAGAGCTTGAGGACATCTTCACGGAGACCGCAGAGGCACA

GGAGCTGGCA

TCTGGCATCGGGGATGCTGCAGAGGCCCGGCGGTGGCTCAGGACCAAGCTGCAGGCGGTGGGAGAAAAAGC

TGGCTTCCCTGGGGTGTTAGACACTGCAAAACCAGGGAAGCTTCATACCATCCCCATCCCTGTCGCCAGGT

GCTACACCTACAGCTGGAGCCAGGACAGCTTTGACATCCTGCAGGAAATCCTGCTCAAGGAACAGGAGCTA

CTCCAGCCAGGGATCCTGGGAGATGATGAAGAGGAGGAAGAGGAGGAGGAGGAGGTGGAGGAGGACTTGGA

AACTGACGGGCACTGTGCCGAGAGAGATTCCCTGCTCTCCACCAGCTCTTTGGCGTCCCATGACTCCACCT

TGTCCCTTGCATCCTCCCAGGCCTCGGGGCCGGCCCTCTCGCGCCATCTGCTGACTTCCTTTGTCTCAGGC

CTCTCTGATGGCATGGACAGCGGCTACGTGGAGGACAGCGAGGAGAGCTCCTCCGAGTGGCCTTGGAGGCG

TGGCAGCCAGGAACGCCGAGGCCACCGCAGGCCTGGGCAGAAGTTCATCAGGATCTATAAACTCTTCAAGA

GCACCAGCCAGCTGGTACTGCGGAGGGACTCTCGGAGCCTGGAGGGCAGCTCGGACACGGCCCTGCCCCTG

AGGCGGGCAGGGAGCCTCTGCAGCCCCTGGACGAACCAGTATCACCCCCTTCCCGGGCCCAGCGCTCCCG

CTCCCTGCCC

CAGCCCAAACTCGGTACCCAGCTGCCCAGCTGGCTTCTGGCCCCTGCTTCACGCCCCAGCGCCGCCGCCC

CTTCCTGAGTGGAGATGAGGATCCCAAGGCTTCCACGCTACGTGTTGTGGTCTTTGGCTCCGATCGGATTT

CAGGGAAGGTGGCTCGGGCGTACAGCAACCTTCGGCGGCTGGAGAACAATCGCCCACTCCTCACACGGTTC

TTCAAACTTCAGTTCTTCTACGTGCCTGTdAAGCGAAGTCGTGGGACCAGCCCTGGTGCCTGTCCACCCCC

TCGGAGCCAGACGCCCTCACCCCCGACAGACTCCCCTAGGCACGCCAGCCCTGGAGAGCTGGGCACCACCC

CATGGGAGGAGAGCACCAATGGCATCTCCCACTACCTCGGCATGCTGGACCCCTGGTATGAGCGCAATGTA

CTGGGCCTCATGCACCTGCCCCCTGAAGTCCTGTGCCAGCAGTCCCTGAAGGCTGAAGCCCAGGCCCTGGA

GGGCTCCCCAACCCAGCTGCCCATCCTGGCTGACATGCTACTCTACTACTGCCGCTTTGCCGCCAGACCGG

TGCTGCTGCAAGTCTATCAGACCGAGCTGACCTTCATCACTGGGGAGAAGACGACAGAGATCTTCATCCAC

TCCTTGGAGCTGGGTCACTCCGCTGCCACACGTGCCATCAAGGCGTCAGGTCCTGGCAGCAAGCGGCTGGG

CATCGATGGC

-continued

```
GACCGGGAGGCTGTTCCTCTAACACTACAGATTATTTACAGCCAGGGGCCATCAGTGGACGAAGTCGCTG
GAGCAACCTGGAGAAGGTCTGTACCTCCGTGAACCTCAACAAGGCCTGCCGGAAGCAGGAGGAGCTGGATT
CCAGCATGGAGGCCCTGACGCTAAACCTGACAGAAdTGGTGAAAAGGCAGAACTCCAAATCCAAGAAGGGC
TTTAACCAGATTAGCACATCGCAGATCAAAGTGGACAAGGTGCAGATCATCGGCTCCAACAGCTGCCCCTT
TGCTGTGTGCCTGGACCAGGATGAGAGAAAGATCCTGCAGAGTGTAGTCAGATGTGAGGTCTCACCGTGCT
ACAAGCCAGAGAAGAGCGACCTCTCCTCACCACCCCAGACGCCTCCTGACCTGCCGGCCCAGGCCGCACCT
GATCTCTGCTCCCTCCTCTGCCTGCCCATCATGACTTTCAGTGGAGCTCTGCCCTAGTGTGGGCCCAGCGC
CAGACTGGACAGAAGCCCTGGGGTCATTTCTCCAGCACTAAAATGGAGTGGAGAGTTGGGGTGGAAATAAG
ACATCCTTAAAAGGTTAAATTGTCTGCAAAGCACCTAGCCCAGTGCCdAGCTCCCAGTAGGTGTTCAGTAA
AGCTTAGTGCCTGACTTTCTGAACACTGATTCCTCCTGTTTGGAGTCACTGGGATACTCTCATTGCCGTTG
GGATGTTCCT
CACTCCTTCCCAGTTCGTGGCTGAGGCAGAACCCAGACTGAAGAGGGAAGAGACATTCCAGAGGAGGATTG
CCTTCGTCAGGGTAAGGGGTGGGCTGCTCAGGGGCCCTACCCTTCACCCCCTTCTGTATCAGATTGGCCCT
CCCACTCCCATCTCACTCTGCGTGTACAATCTTCCATATCCGCAAGTTCACTGGCACTCTTCTGGCACCTG
GGCAAGATCCCAGAACAGAGGATGGAGTGACTGGCCTCACAGAGCTTAGTGCCCGACACTGGTGCATGGGA
AATGGTCAGCCTAGGATAGGACACGAGAGTCTGAAATTCAAAGCAACCAGCTTGAAGTGGTTTGAGAAGCT
GGAAGCAAACATGGGCTAGAGAGATAGGGCAGAAGTCAAGACGAGGATCTGGACTGATGTGGAGAAAGTAG
CCACGGAAGCATGAACTGTATCCTGCACAAAGTCCCTCTTCCCCGCCTCCTAATTCATTATGCCCAAAAGG
CCTTACGTGAAATTCCAGCCCAGAGTACTCATGACTTGAGAGACGTGGACAGAGCCAGCTTCTACCTTGCC
TGGCCGTCTCTCCCCTGTCTTAATGTCTGCTCTTGCTCTAAGCTCCAGAAGAGTGGCGGGCCATGTATCTT
CAATATGTTTTGCTGTATGGGCAGGTTGTCTTATTATGTGATCAACAGATGTCCAGGAACTAATGAGTGG
AATTTAATAT
TATTGTCAAATAAAACTTGATTTGTCCTAT
```

SEQ ID NO:6 (Full-length human p101 protein)

```
MQPGATTCTEDRIQHALERCLHGLSLSRRSTSWSAGLCLNCWSLQELVSRDPGHFLILLEQILQKTREVQE
KGTYDLLTPLALLFYSTVLCTPHFPPDSDLLLKAASTYHRFLTWPVPYCSICQELLTFIDAELKAPGISYQ
RLVRAEQGLPIRSHRSSTVTVLLLNPVEVQAEFLAVANKLSTPGHSPHSAYTTLLLHAFQATFGAHCDVPG
LHCRLQAKTLAELEDIFTETAEAQELASGIGDAAEARRWLRTKLQAVGEKAGFPGVLDTAKPGKLHTIPIP
VARCYTYSWSQDSFDILQEILLKEQELLQPGILGDDEEEEEEEEVEEDLETDGHCAERDSLLSTSSLASH
DSTLSLASSQASGPALSRHLLTSFVSGLSDGMDSGYVEDSEESSSEWPWRRGSQERRGHRRPGQKFIRIYK
LFKSTSQLVLRRDSRSLEGSSDTALPLRRAGSLCSPLDEPVSPPSRAQRSRSLPQPKLGTQLPSWLLAPAS
RPQRRRPFLSGDEDPKASTLRVVVFGSDRISGKVARAYSNLRRLENNRPLLTRFFKLQFFYVPVKRSRGTS
PGACPPPRSQTPSPPTDSPRHASPGELGTTPWEESTNGISHYLGMLDPWYERNVLGLMHLPPEVLCQQSLK
AEAQALEGSPTQLPILADMLLYYCRFAARPVLLQVYQTELTFITGEKTTEIFIHSLELGHSAATRAIKASG
PGSKRLGIDG
DREAVPLTLQIIYSQGAISGRSRWSNLEKVCTSVNLNKACRKQEELDSSMEALTLNLTEVVKRQNSKSKKG
FNQISTSQIKVDKVQIIGSNSCPFAVCLDQDERKILQSVVRCEVSPCYKPEKSDLSSPPQTPPDLPAQAAP
DLCSLLCLPIMTFSGALP
```

What is claimed is:

1. An isolated polynucleotide comprising a polynucleotide sequence which has at least 95% identity to the nucleotide sequence set forth in SEQ ID NO:1, wherein said polynucleotide encodes a polypeptide having p101 regulatory activity towards phosphatidylinositol 3-kinase.

2. The isolated polynucleotide of claim 1 comprising the nucleotide sequence set forth in SEQ ID NO:1.

3. An isolated polynucleotide comprising a polynucleotide sequence encoding a polypeptide which has at least 99% identity to the polypeptide sequence set forth in SEQ ID NO:2, wherein said polypeptide has p101 regulatory activity towards phosphatidylinositol 3-kinase.

4. The isolated polynucleotide of claim 3 comprising a polynucleotide sequence encoding the polypeptide sequence set forth in SEQ ID NO:2.

5. An isolated polynucleotide which is fully complementary to the polynucleotide in any one of claims 1–4 over the entire length of the polynucleotide set forth in such claim.

6. An isolated polynucleotide consisting of a polynucleotide sequence which has at least 95% identity to the nucleotide sequence set forth in SEQ ID NO:3.

7. The isolated polynucleotide of claim 6 consisting of the nucleotide sequence set forth in SEQ ID NO:3.

8. An isolated polynucleotide consisting of a polynucleotide sequence encoding a polypeptide which has at least 95% identity to the amino acid sequence set forth in SEQ ID NO:4.

9. The isolated polynucleotide of claim 8, consisting of a polynucleotide sequence encoding the polypeptide sequence set forth in SEQ ID NO:4.

10. An isolated polynucleotide which is fully complementary to the polynucleotide of any one of claims 6–9 over the entire length of the polynucleotide set forth in such claim.

11. An expression vector comprising a polynucleotide encoding a polypeptide comprising the amino acid sequence of SEQ ID NO:2 when said expression vector is present in a compatible host cell.

12. A process for producing a recombinant host cell comprising the step of introducing the expression vector of claim 11 into a cell such that the host cell, under appropriate culture conditions, produces said polypeptide.

13. A recombinant host cell produced by the process of claim 12.

14. A membrane of a recombinant host cell of claim 13 expressing said polypeptide.

15. A process for producing a polypeptide comprising culturing a host cell of claim 13 under conditions sufficient for the production of said polypeptide and recovering the polypeptide from the culture.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
        (A) LENGTH: 2709 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 1:

```
CCCTTTCCAC CTCTCTGCTC CCATTCCTGA CCCCTTACTT CCCACACCTC TGTCCCGTTC      60

TGCTGCAGGG GTGCTCTGTC CTGCCACTCA GATGTGGCCC TCCAGATGCC ATTCCTACCC     120

TGGAGGCAGC TGTAAGGCCC CTGGTCCTGT TTCCACAGCA CCTGAGCTAT AGCTGGGCTG     180

GGCTGATCGC GCTGCACTGT GAGCACCTGT TGTCTTTACT GGACCAGGTG CTCTCTGGGA     240

AAGGAGCTCG ACAAGCTGAC CGGCGTCTGT CCCCCATGCA GGCGATGACC CAGGATGCAG     300

CCAGGGGCCA CGACATGCAC GGAGGACCGC ATCCAGCATG CCCTGGAACG CTGCCTGCAT     360

GGACTCAGCC TCAGCCGCCG CTCCACCTCC TGGTCAGCTG GGCTGTGTCT GAACTGCTGG     420

AGCCTGCAGG AGCTGGTCAG CAGGGACCCG GGCCACTTCC TTATCCTCCT TGAGCAGATC     480

CTGCAGAAGA CCCGAGAGGT CCAGGAGAAG GGCACCTACG ACCTGCTCAC CCCGCTGGCC     540

CTGCTCTTCT ATTCCACTGT TCTTTGTACA CCACACTTCC CACCAGACTC GGATCTCCTT     600

CTGAAGGCAG CCAGCACCTA CCACCGGTTC CTGACCTGGC CTGTTCCTTA CTGCAGCATC     660

TGCCAGGAGC TGCTCACCTT CATTGATGCT GAACTCAAGG CCCCAGGGAT CTCCTACCAG     720

AGACTGGTGA GGGCTGAGCA GGGCCTGCCC ATCAGGAGTC ACCGCAGCTC CACCACACTG     780

CAAAACCAGG GAAGCTTCAT ACCATCCCCA TCCCTGTCGC CAGGTGCTAC ACCTACAGCT     840

GGAGCCAGGA CAGCTTTGGA GCTGGGCACC ACCCCATGGG AGGAGAGCAC CAATGGCATC     900

TCCCACTACC TCGGCATGCT GGACCCCTGG TATGAGCGCA ATGTACTGGG CCTCATGCAC     960

CTGCCCCCTG AAGTCCTGTG CCAGCAGTCC CTGAAGGCTG AAGCCCAGGC CCTGGAGGGC    1020

TCCCCAACCC AGCTGCCCAT CCTGGCTGAC ATGCTACTCT ACTACTGCCG CTTTGCCGCC    1080

AGACCGGTGC TGCTGCAAGT CTATCAGACC GAGCTGACCT TCATCACTGG GGAGAAGACG    1140

ACAGAGATCT TCATCCACTC CTTGGAGCTG GGTCACTCCG CTGCCACACG TGCCATCAAG    1200

GCGTCAGGTC CTGGCAGCAA GCGGCTGGGC ATCGATGGCG ACCGGGAGGC TGTTCCTCTA    1260

ACACTACAGA TTATTTACAG CCAGGGGGCC ATCAGTGGAC GAAGTCGCTG GAGCAACCTG    1320

GAGAAGGTCT GTACCTCCGT GAACCTCAAC AAGGCCTGCC GGAAGCAGGA GGAGCTGGAT    1380

TCCAGCATGG AGGCCCTGAC GCTAAACCTG ACAGAAGTGG TGAAAAGGCA GAACTCCAAA    1440

TCCAAGAAGG GCTTTAACCA GATTAGCACA TCGCAGATCA AAGTGGACAA GGTGCAGATC    1500

ATCGGCTCCA ACAGCTGCCC CTTTGCTGTG TGCCTGGACC AGGATGAGAG AAAGATCCTG    1560

CAGAGTGTAG TCAGATGTGA GGTCTCACCG TGCTACAAGC AGAGAAGAG CGACCTCTCC    1620

TCACCACCCC AGACGCCTCC TGACCTGCCG GCCCAGGCCG CACCTGATCT CTGCTCCCTC    1680

CTCTGCCTGC CCATCATGAC TTTCAGTGGA GCTCTGCCCT AGTGTGGGCC CAGCGCCAGA    1740

CTGGACAGAA GCCCTGGGGT CATTTCTCCA GCACTAAAAT GGAGTGGAGA GTTGGGGTGG    1800
```

```
AAATAAGACA TCCTTAAAAG GTTAAATTGT CTGCAAAGCA CCTAGCCCAG TGCCGAGCTC    1860

CCAGTAGGTG TTCAGTAAAG CTTAGTGCCT GACTTTCTGA ACACTGATTC CTCCTGTTTG    1920

GAGTCACTGG GATACTCTCA TTGCCGTTGG GATGTTCCTC ACTCCTTCCC AGTTCGTGGC    1980

TGAGGCAGAA CCCAGACTGA AGAGGGAAGA GACATTCCAG AGGAGGATTG CCTTCGTCAG    2040

GGTAAGGGGT GGGCTGCTCA GGGGCCCTAC CCTTCACCCC CTTCTGTATC AGATTGGCCC    2100

TCCCACTCCC ATCTCACTCT GCGTGTACAA TCTTCCATAT CCGCAAGTTC ACTGGCACTC    2160

TTCTGGCACC TGGGCAAGAT CCCAGAACAG AGGATGGAGT GACTGGCCTC ACAGAGCTTA    2220

GTGCCCGACA CTGGTGCATG GGAAATGGTC AGCCTAGGAT AGGACACGAG AGTCTGAAAT    2280

TCAAAGCAAC CAGCTTGAAG TGGTTTGAGA AGCTGGAAGC AAACATGGGC TAGAGAGATA    2340

GGGCAGAAGT CAAGACGAGG ATCTGGACTG ATGTGGAGAA AGTAGCCACG GAAGCATGAA    2400

CTGTATCCTG CACAAAGTCC CTCTTCCCCG CCTCCTAATT CATTATGCCC AAAAGGCCTT    2460

ACGTGAAATT CCAGCCCAGA GTACTCATGA CTTGAGAGAC GTGGACAGAG CCAGCTTCTA    2520

CCTTGCCTGG CCGTCTCTCC CCTGTCTTAA TGTCTGCTCT TGCTCTAAGC TCCAGAAGAG    2580

TGGCGGGCCA TGTATCTTCA ATATGTTTTT GCTGTATGGG CAGGTTGTCT TATTATGTGA    2640

TCAACAGATG TCCAGGAACT AATGAGTGGA ATTTAATATT ATTGTCAAAT AAAACTTGAT    2700

TTGTCCTAT                                                           2709
```

(2) INFORMATION FOR SEQ ID NO: 2:

(i) SEQUENCE CHARACTERISTICS:
        (A) LENGTH: 475 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

```
Met Gln Pro Gly Ala Thr Thr Cys Thr Glu Asp Arg Ile Gln His Ala
 1               5                  10                  15

Leu Glu Arg Cys Leu His Gly Leu Ser Leu Ser Arg Arg Ser Thr Ser
            20                  25                  30

Trp Ser Ala Gly Leu Cys Leu Asn Cys Trp Ser Leu Gln Glu Leu Val
        35                  40                  45

Ser Arg Asp Pro Gly His Phe Leu Ile Leu Leu Glu Gln Ile Leu Gln
50                  55                  60

Lys Thr Arg Glu Val Gln Glu Lys Gly Thr Tyr Asp Leu Leu Thr Pro
65                  70                  75                  80

Leu Ala Leu Leu Phe Tyr Ser Thr Val Leu Cys Thr Pro His Phe Pro
                85                  90                  95

Pro Asp Ser Asp Leu Leu Leu Lys Ala Ala Ser Thr Tyr His Arg Phe
            100                 105                 110

Leu Thr Trp Pro Val Pro Tyr Cys Ser Ile Cys Gln Glu Leu Leu Thr
        115                 120                 125

Phe Ile Asp Ala Glu Leu Lys Ala Pro Gly Ile Ser Tyr Gln Arg Leu
    130                 135                 140

Val Arg Ala Glu Gln Gly Leu Pro Ile Arg Ser His Arg Ser Ser Thr
145                 150                 155                 160

Thr Leu Gln Asn Gln Gly Ser Phe Ile Pro Ser Pro Ser Leu Ser Pro
                165                 170                 175

Gly Ala Thr Pro Thr Ala Gly Ala Arg Thr Ala Leu Glu Leu Gly Thr
```

```
                180             185             190
Thr Pro Trp Glu Glu Ser Thr Asn Gly Ile Ser His Tyr Leu Gly Met
            195             200             205

Leu Asp Pro Trp Tyr Glu Arg Asn Val Leu Gly Leu Met His Leu Pro
210             215             220

Pro Glu Val Leu Cys Gln Gln Ser Leu Lys Ala Glu Ala Gln Ala Leu
225             230             235             240

Glu Gly Ser Pro Thr Gln Leu Pro Ile Leu Ala Asp Met Leu Leu Tyr
            245             250             255

Tyr Cys Arg Phe Ala Ala Arg Pro Val Leu Leu Gln Val Tyr Gln Thr
            260             265             270

Glu Leu Thr Phe Ile Thr Gly Glu Lys Thr Thr Glu Ile Phe Ile His
            275             280             285

Ser Leu Glu Leu Gly His Ser Ala Ala Thr Arg Ala Ile Lys Ala Ser
            290             295             300

Gly Pro Gly Ser Lys Arg Leu Gly Ile Asp Gly Asp Arg Glu Ala Val
305             310             315             320

Pro Leu Thr Leu Gln Ile Ile Tyr Ser Gln Gly Ala Ile Ser Gly Arg
                325             330             335

Ser Arg Trp Ser Asn Leu Glu Lys Val Cys Thr Ser Val Asn Leu Asn
            340             345             350

Lys Ala Cys Arg Lys Gln Glu Glu Leu Asp Ser Ser Met Glu Ala Leu
            355             360             365

Thr Leu Asn Leu Thr Glu Val Val Lys Arg Gln Asn Ser Lys Ser Lys
370             375             380

Lys Gly Phe Asn Gln Ile Ser Thr Ser Gln Ile Lys Val Asp Lys Val
385             390             395             400

Gln Ile Ile Gly Ser Asn Ser Cys Pro Phe Ala Val Cys Leu Asp Gln
                405             410             415

Asp Glu Arg Lys Ile Leu Gln Ser Val Val Arg Cys Glu Val Ser Pro
            420             425             430

Cys Tyr Lys Pro Glu Lys Ser Asp Leu Ser Ser Pro Gln Thr Pro
            435             440             445

Pro Asp Leu Pro Ala Gln Ala Ala Pro Asp Leu Cys Ser Leu Leu Cys
450             455             460

Leu Pro Ile Met Thr Phe Ser Gly Ala Leu Pro
465             470             475

(2) INFORMATION FOR SEQ ID NO: 3:

(i) SEQUENCE CHARACTERISTICS:
        (A) LENGTH: 256 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

TTCCTTACTG CAGCATCTGC CAGGAGCTGC TCACCTTCAT TGATGCTGAA CTCAAGGCCC      60

CAGGGATCTC CTACCAGAGA CTGGTGAGGG CTGAGCAGGG CCTGCCCATC AGGAGTCACC     120

GCAGCTCCAC CGTACACTGC AAAACCAGGG AAGCTCCATG CCATCCCCAT CCCTGTCGCC     180

AGGTGCTACA CCTACAGCTG GAGCCAGGAC AGCTTTGGAG CTGGGCACCA CCCCATGGGA     240

GGAGAGCACC AATGAC                                                     256
```

(2) INFORMATION FOR SEQ ID NO: 4:

(i) SEQUENCE CHARACTERISTICS:
        (A) LENGTH: 84 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

```
Pro Tyr Cys Ser Ile Cys Gln Glu Leu Leu Thr Phe Ile Asp Ala Glu
 1               5                  10                  15

Leu Lys Ala Pro Gly Ile Ser Tyr Gln Arg Leu Val Arg Ala Glu Gln
            20                  25                  30

Gly Leu Pro Ile Arg Ser His Arg Ser Ser Thr Val His Cys Lys Thr
        35                  40                  45

Arg Glu Ala Pro Cys His Pro His Pro Cys Arg Gln Val Leu His Leu
    50                  55                  60

Gln Leu Glu Pro Gly Gln Leu Trp Ser Trp Ala Pro Pro His Gly Arg
65                  70                  75                  80

Arg Ala Pro Met
```

(2) INFORMATION FOR SEQ ID NO: 5:

(i) SEQUENCE CHARACTERISTICS:
        (A) LENGTH: 3630 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

```
ATGCAGCCAG GGGCCACGAC ATGCACGGAG GACCGCATCC AGCATGCCCT GGAACGCTGC     60

CTGCATGGAC TCAGCCTCAG CCGCCGCTCC ACCTCCTGGT CAGCTGGGCT GTGTCTGAAC    120

TGCTGGAGCC TGCAGGAGCT GGTCAGCAGG GACCCGGGCC ACTTCCTTAT CCTCCTTGAG    180

CAGATCCTGC AGAAGACCCG AGAGGTCCAG GAGAAGGGCA CCTACGACCT GCTCACCCCG    240

CTGGCCCTGC TCTTCTATTC CACTGTTCTT TGTACACCAC ACTTCCCACC AGACTCGGAT    300

CTCCTTCTGA AGGCAGCCAG CACCTACCAC CGGTTCCTGA CCTGGCCTGT TCCTTACTGC    360

AGCATCTGCC AGGAGCTGCT CACCTTCATT GATGCTGAAC TCAAGGCCCC AGGGATCTCC    420

TACCAGAGAC TGGTGAGGGC TGAGCAGGGC CTGCCCATCA GGAGTCACCG CAGCTCCACC    480

GTCACCGTGC TGCTGCTGAA CCCAGTGGAA GTGCAGGCCG AGTTCCTTGC TGTAGCCAAT    540

AAGCTGAGTA CGCCCGGACA CTCGCCTCAC AGTGCCTACA CCACCCTGCT CCTGCACGCC    600

TTCCAGGCCA CCTTTGGGGC CCACTGTGAC GTCCCGGGCC TGCACTGCAG GCTACAGGCC    660

AAGACCCTGG CAGAGCTTGA GGACATCTTC ACGGAGACCG CAGAGGCACA GGAGCTGGCA    720

TCTGGCATCG GGATGCTGCA GAGGCCCGG CGGTGGCTCA GGACCAAGCT GCAGGCGGTG    780

GGAGAAAAAG CTGGCTTCCC TGGGGTGTTA GACACTGCAA AACCAGGGAA GCTTCATACC    840

ATCCCCATCC CTGTCGCCAG GTGCTACACC TACAGCTGGA GCCAGGACAG CTTTGACATC    900

CTGCAGGAAA TCCTGCTCAA GGAACAGGAG CTACTCCAGC CAGGGATCCT GGGAGATGAT    960

GAAGAGGAGG AAGAGGAGGA GGAGGAGGTG GAGGAGGACT TGGAAACTGA CGGGCACTGT   1020

GCCGAGAGAG ATTCCCTGCT CTCCACCAGC TCTTTGGCGT CCCATGACTC CACCTTGTCC   1080
```

```
CTTGCATCCT CCCAGGCCTC GGGGCCGGCC CTCTCGCGCC ATCTGCTGAC TTCCTTTGTC    1140

TCAGGCCTCT CTGATGGCAT GGACAGCGGC TACGTGGAGG ACAGCGAGGA GAGCTCCTCC    1200

GAGTGGCCTT GGAGGCGTGG CAGCCAGGAA CGCCGAGGCC ACCGCAGGCC TGGGCAGAAG    1260

TTCATCAGGA TCTATAAACT CTTCAAGAGC ACCAGCCAGC TGGTACTGCG GAGGGACTCT    1320

CGGAGCCTGG AGGGCAGCTC GGACACGGCC CTGCCCCTGA GGCGGGCAGG GAGCCTCTGC    1380

AGCCCCCTGG ACGAACCAGT ATCACCCCCT TCCCGGGCCC AGCGCTCCCG CTCCCTGCCC    1440

CAGCCCAAAC TCGGTACCCA GCTGCCCAGC TGGCTTCTGG CCCCTGCTTC ACGCCCCCAG    1500

CGCCGCCGCC CCTTCCTGAG TGGAGATGAG GATCCCAAGG CTTCCACGCT ACGTGTTGTG    1560

GTCTTTGGCT CCGATCGGAT TCAGGGAAG GTGGCTCGGG CGTACAGCAA CCTTCGGCGG    1620

CTGGAGAACA ATCGCCCACT CCTCACACGG TTCTTCAAAC TTCAGTTCTT CTACGTGCCT    1680

GTGAAGCGAA GTCGTGGGAC CAGCCCTGGT GCCTGTCCAC CCCCTCGGAG CCAGACGCCC    1740

TCACCCCCGA CAGACTCCCC TAGGCACGCC AGCCCTGGAG AGCTGGGCAC CACCCCATGG    1800

GAGGAGAGCA CCAATGGCAT CTCCCACTAC CTCGGCATGC TGGACCCCTG GTATGAGCGC    1860

AATGTACTGG GCCTCATGCA CCTGCCCCCT GAAGTCCTGT GCCAGCAGTC CCTGAAGGCT    1920

GAAGCCCAGG CCCTGGAGGG CTCCCCAACC CAGCTGCCCA TCCTGGCTGA CATGCTACTC    1980

TACTACTGCC GCTTTGCCGC CAGACCGGTG CTGCTGCAAG TCTATCAGAC CGAGCTGACC    2040

TTCATCACTG GGGAGAAGAC GACAGAGATC TTCATCCACT CCTTGGAGCT GGGTCACTCC    2100

GCTGCCACAC GTGCCATCAA GGCGTCAGGT CCTGGCAGCA AGCGGCTGGG CATCGATGGC    2160

GACCGGGAGG CTGTTCCTCT AACACTACAG ATTATTTACA GCCAGGGGGC CATCAGTGGA    2220

CGAAGTCGCT GGAGCAACCT GGAGAAGGTC TGTACCTCCG TGAACCTCAA CAAGGCCTGC    2280

CGGAAGCAGG AGGAGCTGGA TTCCAGCATG GAGGCCCTGA CGCTAAACCT GACAGAAGTG    2340

GTGAAAAGGC AGAACTCCAA ATCCAAGAAG GGCTTTAACC AGATTAGCAC ATCGCAGATC    2400

AAAGTGGACA AGGTGCAGAT CATCGGCTCC AACAGCTGCC CCTTTGCTGT GTGCCTGGAC    2460

CAGGATGAGA GAAAGATCCT GCAGAGTGTA GTCAGATGTG AGGTCTCACC GTGCTACAAG    2520

CCAGAGAAGA GCGACCTCTC CTCACCACCC CAGACGCCTC CTGACCTGCC GGCCCAGGCC    2580

GCACCTGATC TCTGCTCCCT CCTCTGCCTG CCCATCATGA CTTTCAGTGG AGCTCTGCCC    2640

TAGTGTGGGC CCAGCGCCAG ACTGGACAGA AGCCCTGGGG TCATTTCTCC AGCACTAAAA    2700

TGGAGTGGAG AGTTGGGGTG GAAATAAGAC ATCCTTAAAA GGTTAAATTG TCTGCAAAGC    2760

ACCTAGCCCA GTGCCGAGCT CCCAGTAGGT GTTCAGTAAA GCTTAGTGCC TGACTTTCTG    2820

AACACTGATT CCTCCTGTTT GGAGTCACTG GGATACTCTC ATTGCCGTTG GGATGTTCCT    2880

CACTCCTTCC CAGTTCGTGG CTGAGGCAGA ACCCAGACTG AAGAGGGAAG AGACATTCCA    2940

GAGGAGGATT GCCTTCGTCA GGGTAAGGGG TGGGCTGCTC AGGGGCCCTA CCCTTCACCC    3000

CCTTCTGTAT CAGATTGGCC CTCCCACTCC CATCTCACTC TGCGTGTACA ATCTTCCATA    3060

TCCGCAAGTT CACTGGCACT CTTCTGGCAC CTGGGCAAGA TCCCAGAACA GAGGATGGAG    3120

TGACTGGCCT CACAGAGCTT AGTGCCCGAC ACTGGTGCAT GGGAAATGGT CAGCCTAGGA    3180

TAGGACACGA GAGTCTGAAA TTCAAAGCAA CCAGCTTGAA GTGGTTTGAG AAGCTGGAAG    3240

CAAACATGGG CTAGAGAGAT AGGGCAGAAG TCAAGACGAG GATCTGGACT GATGTGGAGA    3300

AAGTAGCCAC GGAAGCATGA ACTGTATCCT GCACAAAGTC CCTCTTCCCC GCCTCCTAAT    3360

TCATTATGCC CAAAAGGCCT TACGTGAAAT TCCAGCCCAG AGTACTCATG ACTTGAGAGA    3420

CGTGGACAGA GCCAGCTTCT ACCTTGCCTG GCCGTCTCTC CCCTGTCTTA ATGTCTGCTC    3480
```

```
TTGCTCTAAG CTCCAGAAGA GTGGCGGGCC ATGTATCTTC AATATGTTTT TGCTGTATGG      3540

GCAGGTTGTC TTATTATGTG ATCAACAGAT GTCCAGGAAC TAATGAGTGG AATTTAATAT      3600

TATTGTCAAA TAAAACTTGA TTTGTCCTAT                                      3630
```

(2) INFORMATION FOR SEQ ID NO: 6:

(i) SEQUENCE CHARACTERISTICS:
        (A) LENGTH: 880 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

```
Met Gln Pro Gly Ala Thr Thr Cys Thr Glu Asp Arg Ile Gln His Ala
 1               5                  10                  15

Leu Glu Arg Cys Leu His Gly Leu Ser Leu Ser Arg Arg Ser Thr Ser
            20                  25                  30

Trp Ser Ala Gly Leu Cys Leu Asn Cys Trp Ser Leu Gln Glu Leu Val
        35                  40                  45

Ser Arg Asp Pro Gly His Phe Leu Ile Leu Leu Glu Gln Ile Leu Gln
50                  55                  60

Lys Thr Arg Glu Val Gln Glu Lys Gly Thr Tyr Asp Leu Leu Thr Pro
65                  70                  75                  80

Leu Ala Leu Leu Phe Tyr Ser Thr Val Leu Cys Thr Pro His Phe Pro
                85                  90                  95

Pro Asp Ser Asp Leu Leu Leu Lys Ala Ala Ser Thr Tyr His Arg Phe
            100                 105                 110

Leu Thr Trp Pro Val Pro Tyr Cys Ser Ile Cys Gln Glu Leu Leu Thr
        115                 120                 125

Phe Ile Asp Ala Glu Leu Lys Ala Pro Gly Ile Ser Tyr Gln Arg Leu
130                 135                 140

Val Arg Ala Glu Gln Gly Leu Pro Ile Arg Ser His Arg Ser Ser Thr
145                 150                 155                 160

Val Thr Val Leu Leu Asn Pro Val Glu Val Gln Ala Glu Phe Leu
                165                 170                 175

Ala Val Ala Asn Lys Leu Ser Thr Pro Gly His Ser Pro His Ser Ala
            180                 185                 190

Tyr Thr Thr Leu Leu Leu His Ala Phe Gln Ala Thr Phe Gly Ala His
        195                 200                 205

Cys Asp Val Pro Gly Leu His Cys Arg Leu Gln Ala Lys Thr Leu Ala
210                 215                 220

Glu Leu Glu Asp Ile Phe Thr Glu Thr Ala Glu Ala Gln Glu Leu Ala
225                 230                 235                 240

Ser Gly Ile Gly Asp Ala Ala Glu Ala Arg Arg Trp Leu Arg Thr Lys
                245                 250                 255

Leu Gln Ala Val Gly Glu Lys Ala Gly Phe Pro Gly Val Leu Asp Thr
            260                 265                 270

Ala Lys Pro Gly Lys Leu His Thr Ile Pro Ile Pro Val Ala Arg Cys
        275                 280                 285

Tyr Thr Tyr Ser Trp Ser Gln Asp Ser Phe Asp Ile Leu Gln Glu Ile
290                 295                 300

Leu Leu Lys Glu Gln Glu Leu Leu Gln Pro Gly Ile Leu Gly Asp Asp
305                 310                 315                 320
```

-continued

```
Glu Glu Glu Glu Glu Glu Glu Val Glu Asp Leu Glu Thr
                325             330             335
Asp Gly His Cys Ala Glu Arg Asp Ser Leu Leu Ser Thr Ser Ser Leu
            340             345             350
Ala Ser His Asp Ser Thr Leu Ser Leu Ala Ser Ser Gln Ala Ser Gly
            355             360             365
Pro Ala Leu Ser Arg His Leu Leu Thr Ser Phe Val Ser Gly Leu Ser
    370             375             380
Asp Gly Met Asp Ser Gly Tyr Val Glu Asp Ser Glu Glu Ser Ser Ser
385             390             395             400
Glu Trp Pro Trp Arg Arg Gly Ser Gln Glu Arg Arg Gly His Arg Arg
            405             410             415
Pro Gly Gln Lys Phe Ile Arg Ile Tyr Lys Leu Phe Lys Ser Thr Ser
            420             425             430
Gln Leu Val Leu Arg Arg Asp Ser Arg Ser Leu Glu Gly Ser Ser Asp
        435             440             445
Thr Ala Leu Pro Leu Arg Arg Ala Gly Ser Leu Cys Ser Pro Leu Asp
    450             455             460
Glu Pro Val Ser Pro Ser Arg Ala Gln Arg Ser Arg Ser Leu Pro
465             470             475             480
Gln Pro Lys Leu Gly Thr Gln Leu Pro Ser Trp Leu Leu Ala Pro Ala
            485             490             495
Ser Arg Pro Gln Arg Arg Pro Phe Leu Ser Gly Asp Glu Pro
            500             505             510
Lys Ala Ser Thr Leu Arg Val Val Phe Gly Ser Asp Arg Ile Ser
            515             520             525
Gly Lys Val Ala Arg Ala Tyr Ser Asn Leu Arg Leu Glu Asn Asn
    530             535             540
Arg Pro Leu Leu Thr Arg Phe Phe Lys Leu Gln Phe Phe Tyr Val Pro
545             550             555             560
Val Lys Arg Ser Arg Gly Thr Ser Pro Gly Ala Cys Pro Pro Arg
            565             570             575
Ser Gln Thr Pro Ser Pro Pro Thr Asp Ser Pro Arg His Ala Ser Pro
            580             585             590
Gly Glu Leu Gly Thr Thr Pro Trp Glu Glu Ser Thr Asn Gly Ile Ser
        595             600             605
His Tyr Leu Gly Met Leu Asp Pro Trp Tyr Glu Arg Asn Val Leu Gly
        610             615             620
Leu Met His Leu Pro Pro Glu Val Leu Cys Gln Gln Ser Leu Lys Ala
625             630             635             640
Glu Ala Gln Ala Leu Glu Gly Ser Pro Thr Gln Leu Pro Ile Leu Ala
            645             650             655
Asp Met Leu Leu Tyr Tyr Cys Arg Phe Ala Ala Arg Pro Val Leu Leu
            660             665             670
Gln Val Tyr Gln Thr Glu Leu Thr Phe Ile Thr Gly Glu Lys Thr Thr
        675             680             685
Glu Ile Phe Ile His Ser Leu Glu Leu Gly His Ser Ala Ala Thr Arg
    690             695             700
Ala Ile Lys Ala Ser Gly Pro Gly Ser Lys Arg Leu Gly Ile Asp Gly
705             710             715             720
Asp Arg Glu Ala Val Pro Leu Thr Leu Gln Ile Ile Tyr Ser Gln Gly
            725             730             735
```

-continued

```
Ala Ile Ser Gly Arg Ser Arg Trp Ser Asn Leu Glu Lys Val Cys Thr
            740             745             750

Ser Val Asn Leu Asn Lys Ala Cys Arg Lys Gln Glu Glu Leu Asp Ser
        755             760             765

Ser Met Glu Ala Leu Thr Leu Asn Leu Thr Glu Val Val Lys Arg Gln
    770             775             780

Asn Ser Lys Ser Lys Lys Gly Phe Asn Gln Ile Ser Thr Ser Gln Ile
785             790             795             800

Lys Val Asp Lys Val Gln Ile Ile Gly Ser Asn Ser Cys Pro Phe Ala
                805             810             815

Val Cys Leu Asp Gln Asp Glu Arg Lys Ile Leu Gln Ser Val Val Arg
            820             825             830

Cys Glu Val Ser Pro Cys Tyr Lys Pro Glu Lys Ser Asp Leu Ser Ser
        835             840             845

Pro Pro Gln Thr Pro Pro Asp Leu Pro Ala Gln Ala Ala Pro Asp Leu
    850             855             860

Cys Ser Leu Leu Cys Leu Pro Ile Met Thr Phe Ser Gly Ala Leu Pro
865             870             875             880
```